(12) United States Patent
Elisseeff et al.

(10) Patent No.: US 8,945,624 B2
(45) Date of Patent: Feb. 3, 2015

(54) PHOTOINITIATED TISSUE FILLER

(75) Inventors: Jennifer H. Elisseeff, Baltimore, MD (US); Alexander Hillel, Baltimore, MD (US); H. Janice Lee, Washington, DC (US)

(73) Assignee: The Johns Hopkins University, Baltimore, MD (US)

( * ) Notice: Subject to any disclaimer, the term of this patent is extended or adjusted under 35 U.S.C. 154(b) by 699 days.

(21) Appl. No.: 12/185,023

(22) Filed: Aug. 1, 2008

(65) Prior Publication Data

US 2009/0074868 A1    Mar. 19, 2009

Related U.S. Application Data

(60) Provisional application No. 60/953,375, filed on Aug. 1, 2007.

(51) Int. Cl.

| | |
|---|---|
| *A61K 9/14* | (2006.01) |
| *A61Q 19/00* | (2006.01) |
| *A61K 8/02* | (2006.01) |
| *A61K 8/81* | (2006.01) |
| *A61L 27/26* | (2006.01) |
| *A61L 27/50* | (2006.01) |

(52) U.S. Cl.
CPC . *A61Q 19/00* (2013.01); *A61K 8/02* (2013.01); *A61K 8/8152* (2013.01); *A61L 27/26* (2013.01); *A61L 27/50* (2013.01); *A61K 2800/81* (2013.01); *A61K 2800/91* (2013.01)
USPC .......................................... 424/486; 424/488

(58) Field of Classification Search
USPC ....................................................... 424/486
See application file for complete search history.

(56) References Cited

U.S. PATENT DOCUMENTS

2004/0225276 A1    11/2004    Burgess
2006/0193899 A1    8/2006    Sawhney

FOREIGN PATENT DOCUMENTS

WO    WO-2006/036681 A2    4/2006

OTHER PUBLICATIONS

Park et al., "Photopolymerized hyaluronic acid-based hydrogels and interpenetrating networks", 2003, Biomaterials, vol. 24, pp. 893-900.*
Summary of Safety and Effectiveness Data for RESTYLANE Injectable Gel, Premarket Approval Application No. P020023, Notice of Approval dated Dec. 12, 2003, pp. 1-13.*
Goldman et al. A Randomized Trial to Determine the Influence of Laser Therapy, Monopolar Radiofrequency Treatment, and Intense Pulsed Light Therapy Administered Imediately after Hyaluronic Acid Gel Implantation. Dermatalogic Surgery, May 2007, vol. 33, No. 5, pp. 535-542, Abstract, para 1-3.
Ross. Laser Versus Intense Pulsed Light: Competing Technologies in Dermatology. Lasers in Surgery and Medicine, 2006, vol. 38, pp. 261-272, p. 265, RHS para 2 and last para; p. 261, RHS para 3, p. 269, Fig 11.
Alster et al. Human Derived and New Synthetic Injectable Materials for Soft Tissue Augmentation: Current Status and Role in Cosmetic Surgery. Plastic & Reconstructive Surgery. Jun. 2000, vol. 105: pp. 2515-2525, p. 2515 LHS para 1; p. 2520, RHS para 1; p. 2517 RHS para 2.

* cited by examiner

*Primary Examiner* — Michael B Pallay
(74) *Attorney, Agent, or Firm* — Johns Hopkins Technology Transfer

(57) ABSTRACT

Visible light-activated polymer cosmetic filler preparations useful in a variety of applications are provided. In some embodiments, the photo-activated polymer composition comprises a conventional polymeric material, such as HA, together with a modified, crosslinkable polymer, such as PEG or PEODA, to permit the formation of crosslinks within the polymer matrix in situ on exposure to a visible light source, such as an IPL device. The preparations provide for a more stabilized composition that is contourable during gelation.

5 Claims, 1 Drawing Sheet

PHOTOINITIATED TISSUE FILLER

This application claims the benefit of U.S. provisional application No. 60/953,375 filed Aug. 1, 2007, which is incorporated herein by reference in its entirety.

BACKGROUND OF INVENTION

Hyaluronic acid (HA), which can be crosslinked, and collagens are biomaterials used in the fields of surgery and dermatology as fillers to recontour/reconstruct tissues. The market of cosmetic fillers for soft tissue augmentation has increased in recent years and there is a need to create longer lasting materials that are retained at the site of application. Physicians also would like to improve control over the final result and allow for subsequent correction to optimize patient satisfaction.

Hydrogels hold the promise of creating dermal fillers that maintain aesthetic corrections longer than currently available fillers. The term, "hydrogel," refers to a broad class of polymeric materials that contain water but do not dissolve in water. Generally hydrogels are cross-linked and networked polymer chains. If there are two or more crosslinks per polymer chain, a network is formed that is able to absorb large amounts of solvent. Hydrogels are of particular interest in the field of tissue engineering because of their tissue-like water content, which allows nutrient and waste transport.

There are a number of methods to form polymers and to crosslink polymers. One such method involves light-reactive reagents and light-induced reactions which create reactive species in a monomer solution, wherein the monomers are polymerized to form chains, monomers, polymers and chains, which in turn can form networks.

Currently used cosmetic fillers are generally derived from biological polymers, such as collagen or hyaluronic acid. Since these compounds are biological in nature, they tend to be sensitive to degradation even if crosslinked. Hence, the esthetic duration of an enhancement/correction achieved with such materials is limited in time, and frequently requires the recipient to undergo additional and expensive repeat injections/treatments to maintain a desired effect. Another drawback of conventional cosmetic fillers is the lack of malleability and contourability to maintain a desired and/or corrective formation after injection, such as, for example, in human cheek bone or chin manipulations. Thus, for these types of and other similar procedures, a more invasive approach is used wherein plastic implants are inserted while a patient is under general anesthesia. Hence, a need continues to exist in the cosmetic reconstructive arts for improved polymeric fillers that are contourable and longer lasting.

Synthetic polymers have highly controllable physical and degradation properties, making them suitable for creating an implant with specific properties. Poly(ethylene glycol), PEG, is an example of a frequently used biocompatible synthetic polymer. PEG, and other synthetic polymers, can be modified to react with functional groups to allow crosslinking and to form hydrogels.

A PEG derivative, poly(ethylene oxide) diacrylate (PEODA), can be injected into the body as a solution and can be polymerized to form a crosslinked, insoluble gel [1-5]. To induce photopolymerization by free radical formation, various photoinitiators have been used. In particular, Hubbell and his colleagues previously created PEODA hydrogels using Eosin Y/triethylamine via argon ion laser (514 nm, 70 mW/cm$^2$, 2 s exposure; American Laser, Salt Lake City) [6]. Eosin Y is a good candidate as a transdermal photoinitiator because of its adsorption range in visible blue light [7,8]. The advantage of visible light, as compared to UV, is that the longer visible wavelength can penetrate deeper into the skin. Moreover, high doses of UV light have been implicated as a cause for erythema and different types of skin cancers [9]. Therefore, photopolymerization using a visible light source would be suitable for the proposed cosmetic applications. Feasibility of PEODA photopolymerization with visible light using Eosin Y as the initiator under human skin, however, is yet to have been established.

Intense pulsed light (IPL) devices are a common visible light source in a dermatology office for photorejuvenation and photoepilation procedures [10-13]. The compatibility of Eosin Y photoinitiation with an IPL device, however, has not been established.

These and other deficiencies in the art of cosmetically useful preparations are satisfied with the present invention.

SUMMARY OF THE INVENTION

In part, the present disclosure provides novel cosmetic fillers activated by visible light that comprise a crosslinkable polymeric material or functional derivatives thereof. The polymers and derivatized polymeric materials may be further described as containing modified reactive groups that facilitate polymerization, attachment and crosslinking of the polymeric material on exposure to light. By exposure to visible light, the liquid form of the synthetic polymer filler in the cosmetic preparation takes on a semisolid or gel form, and is amenable to desired contouring and manipulation to result in a desired, solid and/or semisolid polymerized form in situ. Moreover, the use of derivatized monomers and polymers provides for more stable polymers and networks that are more resistant to biodegradation.

Virtually any polymeric material that may be modified to include a light-activated derivatized reactive group may be used in the preparation of the present cosmetic fillers. By way of example, and not limitation, and in particular embodiments, the polymer can comprise synthetic reactants and comprises poly(ethylene glycol) (PEG) or a derivative thereof. In some embodiments, the polymer derivative comprises poly(ethylene oxide) diacrylate (PEODA) or poly(ethylene glycol) diacrylate (PEGDA).

In another aspect, the invention provides for a method for forming an implant in vivo. In particular embodiments, the method comprises administering a liquid derivatized monomeric material into a desired site in a host, inducing gelation to form a polymeric material by exposing said liquid derivatized monomeric material to light, and contouring said gelling and gelled polymeric material into a desired conformation to provide an implant.

In particular applications, the liquid derivatized polymeric material comprises a combination of a PEODA/Restylene® (a commercially available filler, U.S. Pat. No. 5,827,937) solution. In some embodiments, the PEODA/Restylene® solution comprises 10% PEODA, 15% PEODA, 20% PEODA, 25% PEODA, 30% PEODA, 35% PEODA, 40% PEODA, 45% PEODA, 50% PEODA, 60% PEODA, 70% PEODA or even up to 80% PEODA.

In some embodiments, a photoinitiator is included in the method or in a reagent of the method. In some embodiments, the photoinitiator will be one responsive to visible light, such as one with an absorption maximum in the visible blue light range. An example of such a photoinitiator having an absorption maximum in the visible blue light range is Eosin Y.

In specific applications of the method, a 10% PEODA or a 20% PEODA solution will be used in combination with 200 mM triethylamine and 50 uL/ml Eosin Y initiator.

In some embodiments of the method, the illumination means used is an intense pulsed light (IPL) source. In some embodiments of the method, a combination of Eosin Y/triethylamine and an IPL light source is used to provide a tissue filler or implant. In some embodiments, the illumination means is one wherein the light penetrates the skin, that is, the illumination means is placed above or on the skin, and the visible light is applied to the skin surface.

Compositions of the present disclosure may further comprise a cell, or encapsulated cells, tissues and/or engineered cells and tissues.

The present invention is envisioned to embrace any number of different combinations and concentrations/amounts of synthetic polymers, biodegradable polymers, photoinitiators, proton acceptors, visible light sources and pulse intensity and schedule regimens, and is expected to vary depending on the particular subject being treated, the particular type and location of cosmetic implant/cosmetic filler sought to be achieved, the viscosity and specific physical properties of the cosmetic filler suitable for the specific application being made, as well as other variables associated with clinical procedures of this type known to those of ordinary skill in the cosmetic and medical arts.

One advantage of the present materials/methods is an increased residence/lifetime of fillers and implants in vivo. Another advantage is an improved non-invasive method for providing an implant or filler that may be contoured to a particular subject and/or tissue site in situ. Yet another advantage is the use of visible light which can be applied to the skin surface.

In particular aspects, a composition suitable for tissue augmentation is provided that comprises: (a) modified hyaluronic acid; (b) PEODA; and (c) accelerant of polymerization of the PEODA. Preferably, the PEODA has a molecular weight (e.g. weight average molecular weight) in excess of 2000, 2500, or 3000, with a molecular weight (e.g. weight average molecular weight) of about 3400 being particularly preferred for many applications. Suitable accelerants may include e.g. N-vinyl pyrrolidinone. A particularly preferred modified hyaluronic acid is Restylane™. Such preferred compositions also may suitably comprise an initiator e.g. Eosin Y as well as co-initiator (i.e. a composition that has at least two distinct initiators) such as an amine e.g. a tertiary amine. A trialkyl amine such as triethyl amine or other tri($C_1$-$C_{16}$alkyl)amine can be a preferred co-initiator. In such compositions the weight ratios of PEODA to modified hyaluronic acid can suitably vary rather widely, preferably with PEODA being present in a weight excess relative to the modified hyaluronic acid component, e.g. where the w/w ratio of PEODA:modified hyaluronic acid is from about 2:1 to 10:1. Particularly suitable w/w ratios of PEODA:modified hyaluronic acid include 10:1, 5:1 and 2:1.

In a further particularly preferred aspect, methods are provided for augmenting a soft tissue site comprising: (a) administering to the soft tissue site a composition comprising: PEODA monomers, modified hyaluronic acid, and an accelerant; and (b) applying light to the tissue site to induce polymerization of the PEODA monomers. The soft tissue site is suitably that of a mammal, particularly a primate such as a human, e.g. the neck, orbital groove, breast, cheek and/or nose of such a subject. Suitably the light may be applied externally to the subject. Preferably, such methods also may comprise shaping the soft tissue site by external manipulation. The composition may be administered to the soft tissue site by any of a number of suitable means, such as by injection under the skin. Preferably, the PEODA has a molecular weight (e.g. weight average molecular weight) in excess of 2000, 2500, or 3000, with a molecular weight (e.g. weight average molecular weight) of about 3400 being particularly preferred for many applications. Suitable accelerants may include e.g. N-vinyl pyrrolidinone. A particularly preferred modified hyaluronic acid is Restylane™.

Other aspects of the invention are disclosed infra.

DETAILED DESCRIPTION

Figure 1A:
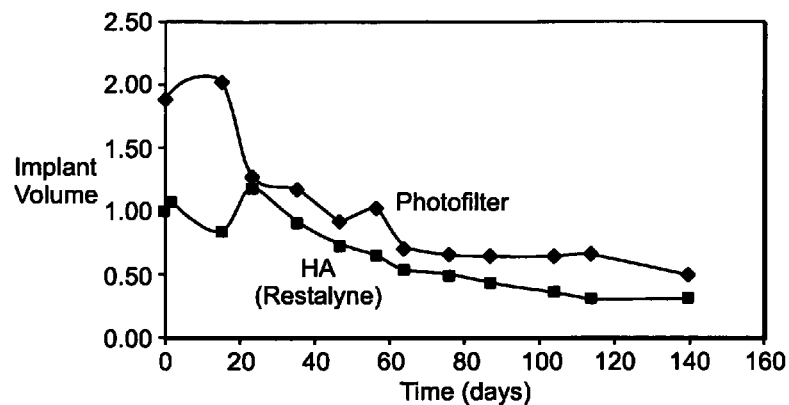
FIGS. 1A and 1B—HA-based filler with PEG crosslinked using light in a subcutaneous space of a mouse retained more volume over the 140 days studied (FIG. 1A). Specific comparison after 28 days (FIG. 1B) defines more clearly the differences between the two groups.

The instant invention relates, in part, to cosmetic and medical polymer-based fillers that form a moldable gel or gel-like composition on photoactivation with a visible light source. The polymer may be naturally occurring or synthetic.

Significant to a product of interest is the advantage of permitting in situ formation of a custom, contoured filler or implant without invasive surgical intervention or general anesthesia. Generally, the product of interest is introduced under the skin (that is, under the epidermis) and polymerization is induced by exposure to visible light applied to the skin surface, that is, from outside of the body or outside of the skin, or to the epidermis.

The instant invention addresses the problem of limited lifetime of cosmetic filler materials, particularly polymeric implantable materials. In some embodiments, the in vivo lifetime of implants and/or other formations made with the present polymer-based preparations, such as PEODA, is increased by 50% or more, such as by 60%, by 70%, by 75%, by 80%, by 85%, by 90% or even up to 100%, compared to conventional implant materials.

The instant invention provides for in situ polymerization techniques to provide cosmetic and medical corrective and/or enhancement procedures using conventional polymeric materials that include a polymer component capable of forming an insoluble crosslinked and crosslinking network on activation with a visible light source.

For example, the instant disclosure provides a cosmetic filler that comprises PEG, or a derivative thereof, such as PEODA, either alone or together with another polymer, such as HA, which may be crosslinked, to provide a cosmetic filler that forms a water insoluble, crosslinked polymer preparation in situ on visible light activation in the presence of a photoinitiator, such as Eosin Y, optionally, in the presence of a proton acceptor, such as, triethylamine.

A biological surface refers to an external (relative to a tissue or organ, for example), exposed portion of a biological material or entity, such as a skin surface, cell, tissue, organ and the like, to which a preparation comprising the light-activated crosslinkable monomer preparation of interest can be exposed or is applied and then said preparation is induced to form a gel in situ on said surface for cosmetic and/or corrective use.

A biologically compatible polymer refers to a polymer which is functionalized to serve as a composition for applying to a biological surface. The polymer is one that is a naturally occurring polymer or one that is not toxic to the host. The polymer may be a homopolymer where all monomers are the same or a heteropolymer containing two or more kinds of monomers. The terms, "biocompatible polymer," "biocompatible cross-linked polymer matrix" and "biocompatibility,"

when used in relation to the instant polymers are art-recognized and are considered equivalent to one another, including, "biologically compatible polymer." For example, biocompatible polymers include polymers that are naturally occurring, or are polymers that can be synthetic, and which are neither toxic to the host (e.g., an animal or human) nor degrade (if the polymer degrades) at a rate or that produces monomeric or oligomeric subunits or other byproducts at toxic concentrations or which are toxic in the host.

In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and overall still be biocompatible and minimally or not toxic.

To determine whether a polymer or other material is biocompatible, it may be necessary to conduct a toxicity analysis. Such assays are well known in the art. One example of such an assay may be performed with live cells, such as HeLa, 293, CHO and the like. The polymer sample is partially or completely degraded as known in the art, using for example, chemical means or enzymatic means. An aliquot of the treated sample products is placed in culture plates previously seeded with the cells. The sample products are incubated with the cells. The results of the assay may be plotted as % relative growth vs. concentration of degraded sample. Non-degraded polymer, monomers, networks and the like can be tested as well.

In addition, monomers, polymers, polymer matrices, and formulations of the present invention may also be evaluated by well-known in vivo tests, such as subcutaneous implantation in rats to confirm that the materials of interest do not cause significant levels of, for example, irritation or inflammation at the subcutaneous implantation sites, An "active agent" and a "biologically active agent" are phrases used interchangeably herein to refer a chemical or biological compound that induces a desired pharmacological or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, it is to be understood that the invention includes the active agent per se, as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Crosslinked herein refers to a composition containing intermolecular links and, optionally, intramolecular links, arising from the formation of covalent bonds. Covalent bonding between two crosslinkable components may be direct, in which case, an atom in one component is directly bound to an atom in the other component, or it may be indirect, that is, for example, through a linking group. A crosslinked gel or polymer matrix may, in addition to covalent bonds, also include intermolecular and/or intramolecular noncovalent bonds such as hydrogen bonds and electrostatic (ionic) bonds.

Functionalized refers to a modification of an existing molecular segment to generate or introduce a new reactive or more reactive group (e.g., an amine, ester or imide group) that is capable of undergoing reaction with another molecule, polymer or functional group (e.g., an amine, an ester or a carboxyl group) to form a covalent bond. For example, carboxylic acid groups can be functionalized by reaction with a carbodiimide and an imide reagent using known procedures to provide a new reactive functional group in the form of an imide group substituting for the hydrogen in the hydroxyl group of the carboxyl function.

Gel refers to a state of matter between liquid and solid, and is generally defined as a polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface). "Gelation time," also referred to herein as "gel time," refers to the time it takes for a composition to become non-flowable under modest stress. This is generally exhibited as reaching a physical state in which the elastic modulus, G', equals or exceeds the viscous modulus, G", i.e., when tan(A) becomes 1 (as may be determined using conventional rheological techniques).

A gel that is "moldable" is one that is conformable to a shape before or during exposure to the light, and which can be contoured or shaped to assume and to retain a particular shape. Thus, following instillation or administration in a space and illumination to catalyze gelation, a composition of interest can be shaped by external manipulation, using, for example, a shaping means, such as, a surgical depressor or other tool or instrument with a flat or curved surface, fingers, the palm, a knuckle and so on.

A hydrogel is a water-swellable polymeric matrix that can absorb water to form elastic gels. Hydrogels consist of hydrophilic polymers crosslinked to from a water-swollen, insoluble polymer network. Crosslinking can be initiated by many physical or chemical mechanisms, for example, such as, a light-induced reaction.

A "matrix" is a three-dimensional network of macromolecules held together by covalent or noncovalent crosslinks. On placement in an aqueous environment, dry hydrogels swell to the extent allowed by the viscosity, the gel state and/or degree of crosslinking in the polymer or network. A matrix can be a network.

Photopolymerization is a method to covalently crosslink polymer chains, whereby a photoinitiator and polymer solution (termed "pre-gel" or monomer solution) are exposed to a light source specific to the photoinitiator. On activation, the photoinitiator reacts with specific functional groups in the polymer chains, linking the functional groups to form the hydrogel. The reaction generally is rapid (3-5 minutes) and can proceed at room or body temperature. Photoinduced gelation enables spatial and temporal control of scaffold formation, permitting shape manipulation after injection and during gelation in vivo. Cells and bioactive factors can be incorporated into the hydrogel scaffold by simply mixing same in and with the polymer solution prior to gelation.

Hydrogels of interest can be semi-interpenetrating networks that promote cell, tissue and organ repair while discouraging scar formation. The hydrogels of interest are derivatized to contain a reactive group to facilitate polymerization and linking. The hydrogels of interest also can carry a reactive group or a functional group reactive with a biological surface, an artificial surface and/or a second polymer or network. The latter form of reactivity also can anchor a gel of interest at and to a site of interest, Hydrogels of interest also are configured to have a viscosity that will enable the gelled hydrogel to remain or reside in place for longer periods of time. Viscosity can be controlled by the monomers and polymers used, the degree of crosslinking, by the level of water trapped in the hydrogel and by incorporated thickeners, such as biopolymers, such as proteins, lipids, saccharides and the like. An example of such a thickener is HA, whether crosslinked or not.

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, comb-burst and starburst polymers.

A monomer is the basic repeating unit in a polymer. A monomer may itself be a monomer or may be dimer or oligomer of at least two same or different monomers, and each dimer or oligomer is repeated in a polymer. A macromer, a macromolecular weight monomer, is generally a polymer or oligomer with a reactive group, often at a terminus, which enables the molecule to act as a monomer.

A polymerizing initiator refers to any substance that can initiate polymerization of monomers or macromers by, for example, free radical generation. The polymerizing initiator often is an oxidizing agent. Exemplary polymerizing initiators include those which are activated by exposure to, for example, electromagnetic radiation, such as visible light.

Certain monomeric subunits of the present invention may exist in particular geometric or stereoisomeric forms. In addition, polymers and other compositions of the present invention may also be optically active. The present invention contemplates all such compounds, including cis-isomers and trans-isomers, R-enantiomers and S-enantiomers, diastereomers, (d)-isomers, (1)-isomers, the racemic mixtures thereof, and other mixtures thereof, as falling within the scope of the invention. Additional asymmetric carbon atoms may be present in a substituent, such as an alkyl group. All such isomers, as well as mixtures thereof, are intended to be included in the invention.

The terms "substituted," "functional group" and "reactive group" are contemplated to include all permissible substituents of organic compounds on the monomers, polymers and networks of interest. In a broad aspect, the permissible substituents include acyclic and cyclic, branched and unbranched, carbocyclic and heterocyclic, aromatic and non-aromatic substituents of organic compounds. Illustrative substituents include, for example, carboxy groups, amine groups, amide groups, hydroxyl groups and so on, as known in the art. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

A functional group or a moiety capable of mediating formation of a polymer or network can be added to a naturally occurring molecule or a synthetic molecule practicing methods known in the art. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrite and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl dials such as butanediol diacrylate and hexanediol diacrylate, divinyl benzene and the like.

It will be understood that substitution or substituted with includes the implicit proviso that such substitution is in accordance with the permitted valency of the substituted atom and the substituent, and that the substitution results in a stable compound, e.g., which does not spontaneously undergo transformation, such as by rearrangement, cyclization, elimination or other reaction.

For purposes of the invention, the chemical elements are identified in accordance with the Periodic Table of the Elements, CAS version, Handbook of Chemistry and Physics, 67th Ed., 1986-87.

In some embodiments, the disclosure is directed to a composition comprising a cosmetic filler generally derived from biological polymers such as collagen or hyaluronic acid. In some embodiments, the polymers are generally linked to produce desired viscosity and physical properties. Those starting molecules are natural components of extracellular matrices. Other suitable polymers include those which also are naturally occurring, such as a glycosaminoglycans, mucopolysaccharides, collagens or proteoglycan components, such as hyaluronic acid, heparin sulfate, glucosamines, dermatans, keratins, heparins, hyalurunan, aggrecan and the like. In general, any biologically compatible polymer can be used as the polymer of interest.

Suitable hydrophilic polymers to serve as polymer of interest include synthetic polymers such as poly(ethylene glycol), poly(ethylene oxide), partially or fully hydrolyzed poly(vinyl alcohol), poly(vinylpyrrolidone), poly(ethyloxazoline), poly (ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers, such as, polysaccharides or carbohydrates such as Ficoll™, polysucrose, dextran, heparan sulfate, chondroitin sulfate or alginate, and polypeptides or proteins such as gelatin, collagen, albumin or ovalbumin, or copolymers or blends thereof. As used herein, "celluloses" includes cellulose and derivatives of the types described above; "dextran" includes dextran and similar derivatives thereof.

In some embodiments, a monomeric unit of a biologically compatible polymer may be functionalized through one or more thio, carboxylic acid or alcohol moieties located on a monomer of the biopolymer. For example, in the case of chondroitin sulfate, a carbonyl group can be derivatized with a imide group using, for example, carbodiimide chemistry. An alcohol group can be derivatized using, for example, the Mitsunobu reaction, Procter et al., Tetra. Lett. 47(29) 5151-5154, 2006.

Polysaccharides that are very viscous liquids or that are thixotropic, and form a gel over time by the slow evolution of structure, are also useful. For example, hyaluronic acid, which can form an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of linking and biodegradation. For example, modified hyaluronic acids may be designed and synthesized to be esterified with a relatively hydrophobic group such as propionic acid or benzylic acid to render the polymer more hydrophobic and gel-forming, or which are grafted with amines to promote electrostatic self-assembly. Modified hyaluronic acids thus, may be synthesized which are injectable, to flow under stress, but maintain a gel-like structure when not under stress. Hyaluronic acid and hyaluronic derivatives are available from Genzyme, Cambridge, Mass. and Fidia, Italy.

Methods for the synthesis of the polymers described above are known to those skilled in the art, see, for example Concise Encyclopedia of Polymer Science and Polymeric Amines and Ammonium Salts, E. Goethals, ed. (Pergamen Press, Elmsford, N.Y. 1980). Many polymers, such as poly(acrylic acid), are commercially available. Naturally occurring polymers can be isolated from biological sources, as known in the art, or are commercially available. Naturally occurring and synthetic polymers may be modified using chemical reactions available in the art and described, for example, in March, "Advanced Organic Chemistry," 4th Edition, 1992, Wiley-Interscience Publication, New York.

Numerous chemical options are available for modifying polymers that may then undergo a radical polymerization. For example, methacrylic anhydride, methacryloyl chloride and glycidyl methacrylate may be used to add methacrylate groups to one or more monomers of a polymer chain. Glycidyl methacrylate may be used, for example, for efficiency of reaction. Further, the modification reagents may be chosen to optimize a lack of cytotoxic byproducts.

A variety of photolabile compounds are available, including, but not limited to, disulfides, benzoins and benzyls for use as a photoinitiator of interest. A non-limiting list of exemplary photoinitiators includes benzophenone, trimethylbenzophenone, thioxanthone, 2-chlorothioxanthone, 9,10-anthraquinone, bis-4,4-dimethylaminobenzophenone, benzoin ethers, benzilketals, α-dialkoxyacetophenones, α-hydroxyalkylphenones, α-amino alkylphenones, acylphosphine oxides, benzophenones/amines, thioxanthones/amines, titanocenes, 2,2-dimethoxy acetophenone, 1-hydroxycyclohexyl phenyl ketone, 2-methyl-1-[4-(methylthio)phenyl]-2-(4-morpholinyl)-1-propanone, 2-hydroxy-1-[4-(hydroxyethoxy)phenyl]-2-methyl-1-propanone, α-hydroxy-ketones and benzilidimethyl-ketals, e.g. Irgacure 651 and 184, and Darocur 1173, marketed by Ciba Chemicals, Rose Bengal, camphorquinone, erythrosine, and mixtures thereof, and so on.

The pregel, monomer solution can comprise a photoinitiator in an amount of, for example, 0.05 to about 1.5% by weight, 0.1 to 1.0% by weight or 0.08 to 0.5% by weight, based on the entire polymerizable component to be gelled, the degree of polymerization and/or networking desired, the rate of polymerization and/or networking desired and so on, as a design choice.

The monomer solution can contain the photoinitiator, the photoinitiator can be mixed with the monomer prior to use or applied separately.

Optionally, a proton acceptor is included. Suitable such proton acceptors are known in the art. An example of such a suitable proton acceptor is an amine, such as a tertiary amine, such as, triethylamine.

An illuminating means can be a light source suitable for activating the photoinitiator used, and which can activate the photoinitiator from outside of the body. While thermal initiators can be used and thus, an infrared source used, and ultraviolet-activated initiators can be used, and thus, a suitable ultraviolet source used, a preferred light source is a white light source. Thus, a suitable photoinitiator is used, such as Eosin Y, so that the maximum absorption of the initiator and the light source are tuned. As mentioned hereinabove, one such visible light source is an IPL device. A commonly used commercially available IPL carries a xenon flash lamp. Other suitable light sources can be used so long as gelation occurs in the body, at the site, under the skin surface and so on, such as, by applying the electromagnetic radiation to the body, to the site as needed, or from above the skin surface. The electromagnetic radiation is applied at an intensity, for a time and for a duration that enables gelation. The light source can be situated above the skin surface or directly on the skin surface.

The monomer solution of interest also can contain any of a variety of other materials, such as, inert materials, such as, preservatives, fillers, excipients or diluents, pharmacologically active molecules or agents, such as a small molecule or a biological, cells and so on, as known in the pharmaceutic arts. Thus, a suitable inert or biologically active agent can be added to the monomer solution. In the case of the latter, the active agent may exert a pharmacologic action locally at the site or in the vicinity of the polymerized or networked structure of interest, or can be released from the formed scaffold, matrix or network to move though the adjoining tissue spaces or may enter the circulatory system for a less local effect.

As discussed above, the functionalized monomer of interest also can be used in combination with other dermatology, orthopedic, cosmetic and so on fillers, patches and so on, such as those which are commercially available. Examples include Restylane[4p], comprising a crosslinked HA, Juvederm (Allergan) comprising HA, Zyderm, comprising collagen, Radiesse™ comprising microspheres in a collagen and so on. Thus, the monomer solution of interest can be mixed with a known filler to provide a composition which is moldable, contourable, has a long residence time and so on.

By way of example, polymer matrix compositions of the invention can be used to block or fill various lumens and voids just below a skin surface. Thus, the instant invention relates to a method of tissue augmentation in a host, such as a human patient, wherein said monomer solution of interest is introduced at a site of interest using methods known in the art, such as injecting a monomer at or in a tissue site in need of augmentation and once applied, exposing the body surface to a visible light to cause polymerization of the deposited monomer solution. A kit containing the injectable monomer, and a delivery means, such as a syringe, as well as an optional light source, a photoinitiator and proton acceptor, is also provided.

"Augmentation" means the repair, prevention or alleviation of defects, particularly defects due to loss or absence of tissue, by providing, augmenting, or replacing such tissue with a polymer or network or interest. Augmentation is also meant to include supplementation of a natural structure or feature, that is, a building of adding to an existing body part, for example, to increase the size thereof, such a lips, nose, breast, ears, portions of the reproductive organs, eyebrows, chin, cheeks and so on. While the invention is designed primarily for soft tissue augmentation, hard tissue augmentation is encompassed as the injectable compositions of the invention can be applied to a hard tissue and can be used in combination with, for example, materials to promote mineralization or bone formation. Thus, tissue augmentation can include the filling of lines, folds, wrinkles, minor facial depressions, cleft lips, superficial wrinkles and the like, such as, in the face and neck; the correction of minor deformities due to aging or disease, including in the hands and feet, fingers and toes; the augmentation of the vocal cords or glottis to rehabilitate speech; the dermal filling of sleep lines and expression lines; the replacement of dermal and subcutaneous tissue lost due to aging; the augmentation of lips; the filling of wrinkles and the orbital groove around the eye; the augmentation of the breast; the augmentation of the chin; the augmentation of the cheek and/or nose; the filling of indentations in soft tissue, dermal or subcutaneous, due to, e.g., overzealous liposuction or other trauma; the filling of acne or traumatic scars and rhytids; the filling of nasolabial lines, nasoglabellar lines and infraoral lines and so on.

The monomer solution of interest is one which has a viscosity suitable for ready extrusion through a delivery means, such as a fine surgical needle (e.g., needles having a gauge of at least 22, at least 27 or finer) at the temperature of use. Thus, a solution that is, "injectable" is one having a texture and viscosity which permits flow through a suitable delivery device, such as, a surgical needle, other surgical instrument, or other delivery means such as a equipment used in endoscopic or percutaneous discectomy procedures, by employing typical injection pressures. The monomer solution of interest thus is injectable through a suitable applicator, such as a catheter, a cannula, a needle, a syringe, tubular apparatus and so on, as known in the art.

The viscosity of the monomer solution can be varied as a design choice to suit the intended use. For example, for application to superficial sites or little tissue space volume, a less viscous monomer solution can be used to ensure flowability of the solution. In other sites, such as larger tissue spaces or deeper sites, a more viscous monomer solution can be used to facilitate retention of the monomer solution at the site prior to and during exposure to the photoinitiator and light.

The instant invention also provides kits for enabling performing the method of the invention. Such kits can be prepared from readily available materials and reagents and can come in a variety of embodiments as known in the pharmaceutic and medical arts. For example, such kits can comprise, in an amount sufficient for at least one treatment, a photoactivatable monomer solution, optionally, sterilized buffers or water, other reagents necessary or helpful to perform the method, and instructions. Instructions include a tangible expression describing reagent concentration or at least one method parameter, such as the amount of reagent to be used, stability conditions of the reagent(s) and the like, to allow the user to carry out the method of the instant invention. In one embodiment, a kit comprises a means for delivery in which is placed a monomer of interest, which often is pre-sterilized. Such delivery means can include, by way of illustration and not limitation, a small syringe (for example, 22 to 27 gauge), a large syringe (for example, 13 to 19 gauge) or equipment used in endoscopic or percutaneous discectomy procedures. The delivery means can be pre-sterilized and encased in a sterile containing means, such as a plastic wrapper. The reagents can be provided in solution, as suspensions, or as a substantially dry powder, e.g., in lyophilized form, either independently or in a mixture of components to improve ease of use and stability. Where a degradable reagent is provided, conditions are selected which maximize stability of the reagent(s), e.g., storage at lower temperature, addition of stabilizing agents (e.g., glycerol or a reducing agent) and so on, as known in the art. Unstable reagents can be provided together with or separately from the more stable components of the kit. The reagents and instructions can be placed and carried in a container means for immobilizing the reagents therein thereby providing support and protection for the contents, providing stackability of units, providing insulation, providing a transporting form and so on.

The reagents are manufactured, kitted, stored and so on in a manner acceptable in the pharmaceutic arts, practicing methods and using reagents that are suitable for in vivo use, as known in the art, see for example, Remington: The Science and Practice of Pharmacy, latest edition.

The invention now being generally described, it will be more readily understood by reference to the following examples which are included merely for purposes of illustration of certain aspects and embodiments of the present invention, and are not intended to limit the invention.

Example 1

Dermal Filler Comprising PEG and HA

The present example demonstrates the utility of the present invention for providing a light-activated injectable cosmetic filler comprising a modified crosslinkable polymer together with HA.

A range of concentrations of PEG in HA filler (Restylane®) were examined. A blue dye was incorporated in the PEG to better visualize the implant and the degradation thereof. Without PEG present, the HA quickly dissolved in the buffer solution. As more PEG was added to the filler, the shape (and incorporated dye) was maintained longer.

Figure 1B:
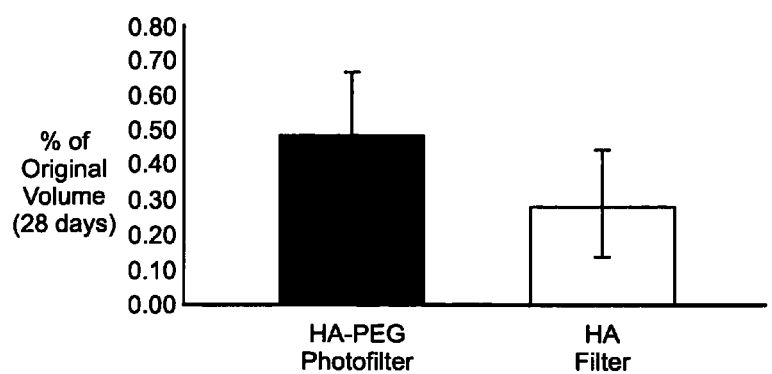

A suitable obtained concentration of PEG-HA was then translated to in vivo studies, which demonstrated that incorporation of a crosslinked polymer with a commercially available dermal filler extended the lifetime of that filler. The data summarized and presented in FIG. 1 demonstrated an enhanced retention of a dermal photofiller, that includes a combination of HA (Restylane) and PEG, by almost 100%, compared to HA (Restylane®) alone.

Example 2

Cosmetic Filler Comprising PEODA and HA

The present example demonstrates the utility of the present invention for providing a cosmetic filler composition that comprises HA and PEODA.

A number of polymer combinations were tested including varying polymer concentrations and compositions. Those factors can play a role in the monomer properties, such as viscosity, crosslinking density and subsequent swelling and mechanical properties of the hydrogel.

Macromer solutions: PEODA/HA (Restylene®) macromer solution was prepared by mixing 200 mM triethylamine (Sigma Aldrich), 50 pl/mL Eosin Y (Sigma Aldrich), N-vinylpyrrolidone (Sigma Aldrich), and PEODA (SunBio, Seoul, South Korea, molecular weight: 3400 g/mol) in Restylene®. Three different concentrations of PEODA were used: 4 and 10% PEODA and 20% 4-arm PEODA.

Then, the macromer solution was injected under the skin of a 78 year-old female cadaver and was photopolymerized by IPL exposure (intensity per pulse, ~5 J/cm$^2$) under three different conditions.

Subcutaneous mold: Macromer solution of approximately 100 pL was put in a mold and placed under the skin. IPL light was shone, and the number of IPL pulses required for polymerization of macromer solution was counted and recorded (Table 1).

Dermal pocket: Under the skin, a constrained space with a smooth surface was created, and macromer solution of approximately 500 pL was placed in the pocket without a mold. IPL light was shone, and the number of IPL pulses required for polymerization of macromer solution was counted and recorded (Table 1).

Intradermal injection: Macromer solution was injected under the skin.

Solidification of the macromer solutions was observed after different IPL pulses were applied. Polymerization was confirmed following excision of the site.

The distance from which the IPL light source was held from the skin had an effect on polymerization, and macromer solutions were not polymerized if the IPL source was held further than approximately 3 cm from the cadaver skin surface. Therefore, the IPL light source was kept about 1 cm from the skin, and the amount of energy required for photopolymerization of macromer solutions was determined (Table 1). The results indicated that the PEODA/Restylene® macromer solution indeed can be polymerized in dermal and intradermal spaces using Eosin Y initiator and IPL light source.

TABLE 1

| Group | Procedure | Pulses (5 J/cm$^2$ per) | Total (J/cm$^2$) | Polymerization |
|---|---|---|---|---|
| Restylene ® + 10% PEODA | Subcutaneous Mold | 12 | 60 | + |
| | Dermal Pocket | 10 | 50 | + |
| | Intradermal Injection | 18 | 90 | + |
| Restylene ® + 4% PEODA | Subcutaneous Mold | 12 | 60 | + |
| | Dermal Pocket | 14 | 70 | + |
| | | 18 | 90 | |
| | Intradermal Injection | 30 | 150 | + |
| Restylene + 20% 4 arm PEODA | Subcutaneous Mold | 8 | 40 | + |
| | Dermal Pocket | 6 | 30 | + |
| | Intradermal Injection | 10 | 50 | + |

All publications and patents mentioned herein are hereby incorporated by reference in their entirety as if each individual publication or patent was specifically and individually indicated to be incorporated by reference.

BIBLIOGRAPHY

The following references are specifically incorporated herein in their entirety by reference.

1. Elisseeff J, Anseth K, Sims D, McIntosh W, Randolph M, Langer R: Transdermal photo polymerization for minimally invasive implantation. Proc Natl Acad Sci USA 1999; 96:3104-3107.
2. Williams C G, Kim T K, Taboas A, Malik A, Manson P, Elisseeff J: In vitro chondrogenesis of bone marrow-derived mesenchymal stem cells in a photopolymerizing hydrogel. Tissue Eng 2003; 9:679-688.
3. Elisseeff J: Injectable cartilage tissue engineering. Expert Opin Biol Ther 2004; 4:1849-1859.
4. Elisseeff J, Anseth K, Sims D, McIntosh W, Randolph M, Yaremchuk M, Langer R: Transdermal photo polymerization of poly(ethylene oxide)-based injectable hydrogels for tissue-engineered cartilage. Plast Reconstr Surg 1999; 104:1014-1022.
5. Nguyen K T, West J L: Photopolymerizable hydrogels for tissue engineering applications. Biomaterials 2002; 23:4307-4314.
6. Hill-West J L, Chowdhury S M, Slepian M J, Hubbell J A: Inhibition of thrombosis and intimal thickening by in situ photopolymerization of thin hydrogel barriers. Proc Natl Acad Sci USA 1994; 91:5967-5971.
7. Nakayama Y, Matsuda T: Photocurable surgical tissue adhesive glues composed of photo reactive gelatin and poly (ethylene glycol) diacrylate. Blamed Mater Res 1999; 48:511-521.
8. Valdesaguilera O, Pathak C, Shi J, Watson D, Neckers D: Photopolymerization studies using visible light photoinitiators. Macro 1992; 25:541-547.
9. Levine J A, Sorace M, Spencer J, Siegel D M: The indoor UV tanning industry: a review of skin cancer risk, health benefit claims, and regulation. J Am Acad Dermatol 2005; 53:1038-1044.
10. Marayiannis K B, Vlachos S P, Savva M P, Kontoes P P: Efficacy of long- and short pulse alexandrite lasers compared with an intense pulsed light source for epilation: a study on 532 sites in 389 patients. J Cosmet Laser Ther 2003; 5:140-145.
11. Negishi K, Kushikata N, Takeuchi K, Tezuka Y, Wakamatsu S: Photorejuvenation by intense pulsed light with objective measurement of skin color in Japanese patients. Dermatol Surg 2006; 32:1380-1387.
12. Goldman M P, Weiss R A, Weiss M A: Intense pulsed light as a nonablative approach to photoaging. Dermatol Surg 2005; 31:1179-1187; discussion 1187.
13. Sadick N S, Weiss R, Kilmer S, Bitter P: Photorejuvenation with intense pulsed light: results of a multi-center study. J Drugs Dermatol 2004; 3:41-49.

We claim:

1. A method of filling a tissue space under the epidermis comprising:
   a) introducing a polymer solution into the tissue space comprising:
      i) a modified hyaluronic acid consisting of a Non Animal Stabilized Hyaluronic Acid having a molecular weight of about 1 million, and stabilized by 1,4-Butanediol Diglycidyl Ether (BDDE);
      ii) PEGDA and/or PEODA having a molecular weight of between about 2000 to 3400 daltons;
      iii) N-vinyl pyrrolidinone;
      iv) at least one initiator;
   wherein the ratio of PEGDA and/or PEODA to modified hyaluronic acid in w/w is from about 5:1 to 10:1; and b) applying visible light to the surface of the epidermis superficial to said space to induce polymerization.

2. The method of claim 1, wherein said visible light is provided by an IPL device.

3. The method of claim 2, wherein said device is placed 1 cm above the epidermis.

4. The method of claim 2, wherein said device is placed on the epidermis.

5. The method of claim 2, wherein the PEGDA and/or PEODA has a molecular weight of about 3400.

* * * * *